United States Patent
Okabe

(10) Patent No.: US 9,943,537 B2
(45) Date of Patent: Apr. 17, 2018

(54) ANTITUMOR AGENT AND ANTITUMOR EFFECT ENHANCER

(71) Applicant: TAIHO PHARMACEUTICAL CO., LTD., Chiyoda-ku (JP)

(72) Inventor: Hiroyuki Okabe, Hanno (JP)

(73) Assignee: TAIHO PHARMACEUTICAL CO., LTD., Chiyoda-ku (JP)

(*) Notice: Subject to any disclaimer, the term of this patent is extended or adjusted under 35 U.S.C. 154(b) by 0 days.

(21) Appl. No.: 14/916,878

(22) PCT Filed: Sep. 5, 2014

(86) PCT No.: PCT/JP2014/073436
§ 371 (c)(1),
(2) Date: Mar. 4, 2016

(87) PCT Pub. No.: WO2015/034032
PCT Pub. Date: Mar. 12, 2015

(65) Prior Publication Data
US 2016/0193241 A1 Jul. 7, 2016

(30) Foreign Application Priority Data
Sep. 6, 2013 (JP) ................................. 2013-184684

(51) Int. Cl.
| | |
|---|---|
| *A61K 39/395* | (2006.01) |
| *A61K 31/7072* | (2006.01) |
| *A61K 31/513* | (2006.01) |
| *C07K 16/22* | (2006.01) |
| *C07K 16/28* | (2006.01) |
| *A61K 39/00* | (2006.01) |

(52) U.S. Cl.
CPC ........ *A61K 31/7072* (2013.01); *A61K 31/513* (2013.01); *A61K 39/395* (2013.01); *A61K 39/39533* (2013.01); *C07K 16/22* (2013.01); *C07K 16/2863* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 5,744,475 A | 4/1998 | Yano et al. | |
| 6,159,969 A | 12/2000 | Yano et al. | |
| 6,294,535 B1 | 9/2001 | Yano et al. | |
| 7,312,243 B1 * | 12/2007 | Pravda | A61K 31/12 424/653 |

FOREIGN PATENT DOCUMENTS

| | | |
|---|---|---|
| EP | 2 979 700 A1 | 2/2016 |
| EP | 2 979 701 A1 | 2/2016 |
| WO | 96 30346 | 10/1996 |
| WO | 2014 157443 A1 | 9/2001 |
| WO | 2014 157444 A1 | 10/2014 |

OTHER PUBLICATIONS

Y. Kuroboki, et al., "A Multicenter, Randomized, Double-blind, Phase II Study TAS-102 (A) Plus Best Supportive Care (BSC) Versus Placebo (P) Plus BSC in Patients (pts) With Chemotherapy-refractory Metastatic Colorectal Cancer (mCRC)", European Journal of Cancer, vol. 47, 2011, 2 pages.
Irene V. Bijnsdorp, et al., "Molecular mechanism underlying the synergistic interaction between trifluorothymidine and the epidermal growth factor receptor inhibitor erlotinib in human colorectal cancer cell lines", Cancer Sci., vol. 101, No. 2, 2010, pp. 440-447.
Olaf H. Temmink, et al., "Therapeutic potential of the dual-targeted TAS-102 formulation in the treatment of gastrointestinal malignancies", Cancer Sci., vol. 98, No. 6, 2007, pp. 779-789.
Olaf H. Temmink, et al., "Irinotecan-induced cytotoxicity to colon cancer cells in vitro is stimulated by pre-incubation with trifluorothymidine", European Journal of Cancer, vol. 43, No. 1, 2007, pp. 175-183.
Takayuki Yoshino, et al., "TAS-102 monotherapy for pretreated metastatic colorectal cancer: a double-blind, randomised, placebo-controlled phase 2 trial", Lancet Oncol, vol. 13, No. 10, 2012, pp. 993-1001.
Michael J. Overman, et al., "Phase 1 study of TAS-102 administered once daily on a 5-day-per-week schedule in patients with solid tumors", Invest New Drugs, vol. 26, No. 5, 2008, pp. 445-454.
Oh Temmink, et al., "Mechanism of trifluorothymidine potentiation of oxaliplatin-induced cytotoxicity to colorectal cancer cells", British Journal of Cancer, vol. 96, No. 2, 2007, pp. 231-240.
Taher, Abu-Hejleh, et al., "Incidence and Management of Gastrointestinal Perforation from Bevacizumab in Advanced Cancers", Curr Oncol Rep, vol. 14, No. 4, 2012, pp. 277-284.
B. Vincenzi, et al., "CETUXIMAB: From Bench to Bedside", Current Cancer Drug Targets, vol. 10, No. 1, 2010, pp. 80-95.
Laszlo Kopper, "Panitumumab: An Arrow on Target", Pathol. Oncol. Res., vol. 16, No. 2, 2010, pp. 143-148.
International Search Report dated Nov. 11, 2014, in PCT/JP2014/073436 Filed Sep. 5, 2014.

* cited by examiner

*Primary Examiner* — Sheela J Huff
(74) *Attorney, Agent, or Firm* — Oblon, McClelland, Maier & Neustadt, L.L.P.

(57) ABSTRACT

Provided is a novel method for treating a cancer using an FTD/TPI combination drug, which shows remarkably excellent antitumor effect and small adverse effects.
An antitumor agent, in which a combination drug containing trifluridine and tipiracil hydrochloride at a molar ratio of 1:0.5 and an anti-VEGF antibody or anti-EGFR antibody are administered in combination.

20 Claims, 9 Drawing Sheets

ANTITUMOR AGENT AND ANTITUMOR EFFECT ENHANCER

CROSS REFERENCE TO RELATED APPLICATION

This application is a National Stage entry under 35 USC 371 of PCT/JP2014/073436, filed on Sep. 5, 2014, and claims priority to Japanese Patent Application No. 2013-184684, filed on Sep. 6, 2013, the entireties of which are both incorporated herein by reference.

TECHNICAL FIELD

The present invention relates to an antitumor agent containing a combination drug of trifluridine and tipiracil hydrochloride, and an anti-VEGF antibody or anti-EGFR antibody, and an antitumor effect enhancer of an anti-VEGF antibody or anti-EGFR antibody.

BACKGROUND ART

Trifluridine (also known as α,α,α-trifluorothymidine. Hereinafter, also referred to as "FTD") manifests antitumor effects by DNA synthesis inhibition from an action of inhibiting thymidylate production and by DNA function blocking from incorporation into DNA. Meanwhile, tipiracil hydrochloride (chemical name: 5-chloro-6-[(2-iminopyrrolidine-1-yl)methyl]pyrimidine-2,4(1H,3H)-dione hydrochloride. Hereinafter, also referred to as "TPI") has an action of inhibiting thymidine phosphorylase. It is known that antitumor effect of FTD is enhanced by TPI that suppresses in vivo decomposition of FTD by thymidine phosphorylase (Patent Literature 1). Currently, an antitumor agent containing FTD and TPI at a molar ratio of 1:0.5 (hereinafter, also referred to as an "FTD/TPI combination drug") is under development as a therapeutic agent for a solid cancer such as colorectal cancer (Non-Patent Literatures 1 and 2).

Furthermore, combination therapies to enhance the antitumor effect of an FTD/TPI combination drug have been studied, and the combined effect of the combination drug and irinotecan and oxaliplatin have been suggested so far (Non-Patent Literatures 3 and 4).

Meanwhile, in recent years, development of a drug targeting a molecule involved in angiogenesis or cell proliferation such as Vascular Endothelial Growth Factor (hereinafter, VEGF) and Epidermal Growth Factor Receptor (hereinafter, EGFR) is actively performed. For example, as a molecular target drug for VEGF, bevacizumab, which is an anti-VEGF humanized monoclonal antibody, is clinically used as a therapeutic agent for a carcinoma such as colorectal cancer, non-small cell lung cancer, breast cancer and renal cell cancer. In addition, as a molecular target drug for EGFR, cetuximab, which is an anti-EGFR human/mouse chimeric monoclonal antibody, is clinically used as a therapeutic agent for colorectal cancer and head and neck cancer, and panitumumab, which is an anti-EGFR human-type fully monoclonal antibody, is clinically used as a therapeutic agent for colorectal cancer, respectively (Non-Patent Literatures 5, 6 and 7).

As described above, although developments of a therapy including an FTD/TPI combination drug are energetically performed, a combination therapy using an FTD/TPI combination drug and a molecular target drug for VEGF or EGFR, is not known at all.

CITATION LIST

Patent Literature

Patent Literature 1: WO 96/30346 A

Non-Patent Literatures

Non-Patent Literature 1: Invest New Drugs 26(5): 445-54, 2008.
Non-Patent Literature 2: Lancet Oncol. 13(10): 993-1001, 2012.
Non-Patent Literature 3: Eur J Cancer. 43(1): 175-83, 2007.
Non-Patent Literature 4: Br J Cancer. 96(2): 231-40, 2007.
Non-Patent Literature 5: Curr Oncol Rep. 14(4): 277-84, 2012.
Non-Patent Literature 6: Curr Cancer Drug Targets. 10(1): 80-95, 2010.
Non-Patent Literature 7: Pathol Oncol Res. 16(2): 143-8, 2010.

SUMMARY OF INVENTION

Technical Problem

An object of the present invention is to provide a novel method for treating a cancer using an FTD/TPI combination drug, which shows remarkably excellent antitumor effect and less adverse effects.

Solution to Problem

In consideration of such situations, the present inventors found that concomitant use of an FTD/TPI combination drug and an anti-VEGF antibody or anti-EGFR antibody suppresses occurrence of adverse effects and remarkably enhances the antitumor effect of the anti-VEGF antibody or anti-EGFR antibody.

That is, the present invention provides the following [1] to [21].

[1] An antitumor agent, wherein a combination drug containing trifluridine and tipiracil hydrochloride at a molar ratio of 1:0.5 and an anti-VEGF antibody or anti-EGFR antibody are administered in combination.
[2] The antitumor agent according to [1], wherein the anti-VEGF antibody is bevacizumab.
[3] The antitumor agent according to [1] or [2], wherein the anti-EGFR antibody is cetuximab or panitumumab.
[4] The antitumor agent according to any one of [1] to [3], wherein target cancer is colorectal cancer, lung cancer, breast cancer, pancreatic cancer, or gastric cancer.
[5] An antitumor effect enhancer including a combination drug containing trifluridine and tipiracil hydrochloride at a molar ratio of 1:0.5 for enhancing the antitumor effect of an anti-VEGF antibody or anti-EGFR antibody.
[6] An antitumor agent including a combination drug containing trifluridine and tipiracil hydrochloride at a molar ratio of 1:0.5 for treating a cancer patient administered with an anti-VEGF antibody or anti-EGFR antibody.
[7] A kit preparation including a combination drug containing trifluridine and tipiracil hydrochloride at a molar ratio of 1:0.5, and an instruction manual, wherein the instruction manual describes that the combination drug containing trifluridine and tipiracil hydrochloride at a molar ratio of 1:0.5 is administered in combination with the anti-VEGF antibody or anti-EGFR antibody to a cancer patient.

[8] A combination drug containing trifluridine and tipiracil hydrochloride at a molar ratio of 1:0.5 for enhancing the antitumor effect of an anti-VEGF antibody or anti-EGFR antibody.

[9] A combination drug containing trifluridine and tipiracil hydrochloride at a molar ratio of 1:0.5 for treating a cancer patient administered with an anti-VEGF antibody or anti-EGFR antibody.

[10] The combination drug according to [8] or [9], wherein the anti-VEGF antibody is bevacizumab.

[11] The combination drug according to any one of [8] to [10], wherein the anti-EGFR antibody is cetuximab or panitumumab.

[12] The combination drug according to any one of [8] to [11], wherein target cancer is colorectal cancer, lung cancer, breast cancer, pancreatic cancer, or gastric cancer.

[13] Use of a combination drug containing trifluridine and tipiracil hydrochloride at a molar ratio of 1:0.5 for producing an antitumor effect enhancer enhancing the antitumor effect of an anti-VEGF antibody or anti-EGFR antibody.

[14] Use of a combination drug containing trifluridine and tipiracil hydrochloride at a molar ratio of 1:0.5 for producing an antitumor agent for a cancer patient administered with an anti-VEGF antibody or anti-EGFR antibody.

[15] The use according to [13] or [14], wherein the anti-VEGF antibody is bevacizumab.

[16] The use according to any one of [13] to [15], wherein the anti-EGFR antibody is cetuximab or panitumumab.

[17] The use according to any one of [13] to [16], wherein the target cancer is colorectal cancer, lung cancer, breast cancer, pancreatic cancer, or gastric cancer.

[18] A method for treating a cancer, including administering a combination drug containing trifluridine and tipiracil hydrochloride at a molar ratio of 1:0.5 and an anti-VEGF antibody or anti-EGFR antibody in combination.

[19] The method according to [18], wherein the anti-VEGF antibody is bevacizumab.

[20] The method for treating according to [18], wherein the anti-EGFR antibody is cetuximab or panitumumab.

[21] The method for treating according to any one of [18] to [20], wherein target cancer is colorectal cancer, lung cancer, breast cancer, pancreatic cancer, or gastric cancer.

Advantageous Effects of Invention

According to the antitumor agent of the present invention, it is possible to perform a cancer treatment suppressing outbreak of adverse effects and exerting high antitumor effect, and thus bring long time survival of a cancer patient.

DESCRIPTION OF EMBODIMENTS

Figure 1:
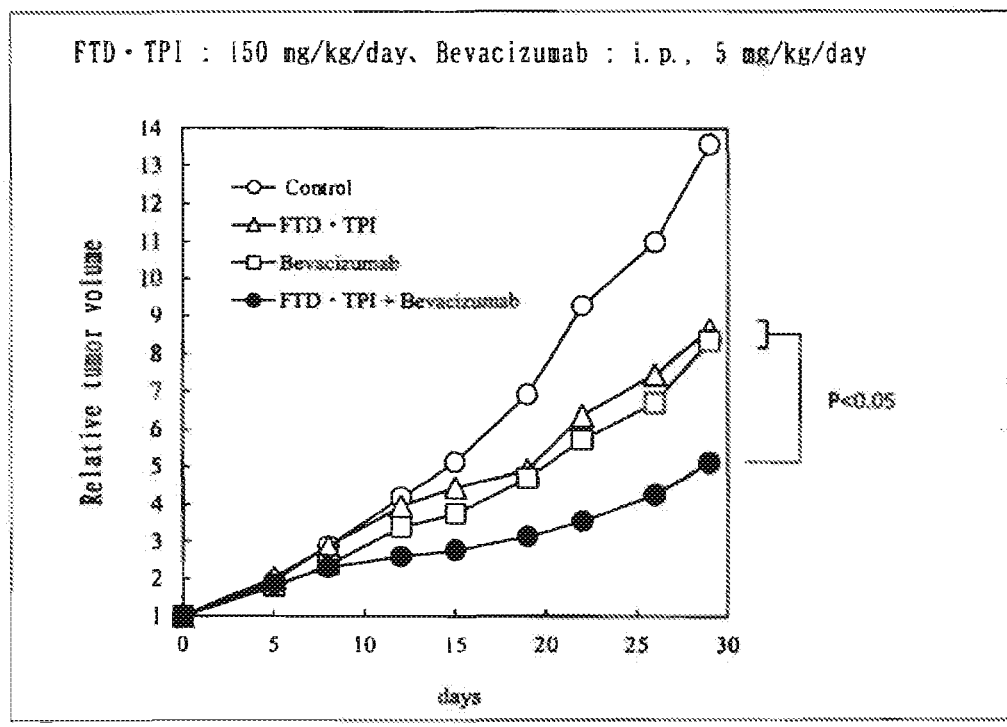
FIG. 1 is a figure illustrating the combinatorial effect of an FTD/TPI combination drug and bevacizumab with respect to colon cancer.
Figure 2:
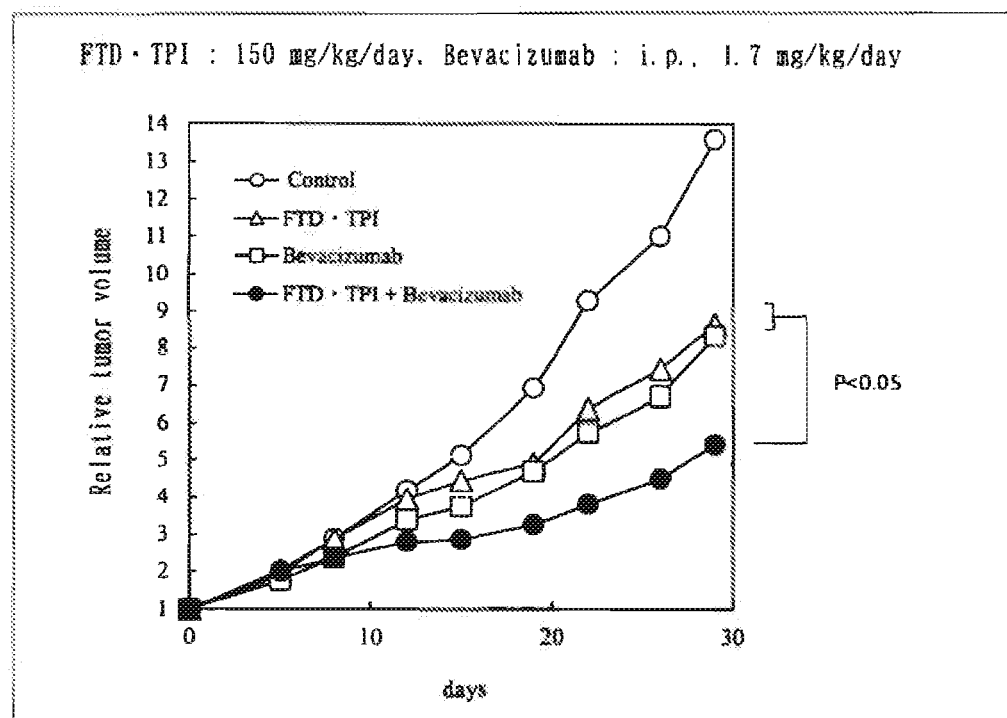
FIG. 2 is a figure illustrating the combinatorial effect of an FTD/TPI combination drug and bevacizumab with respect to colon cancer.
Figure 3:
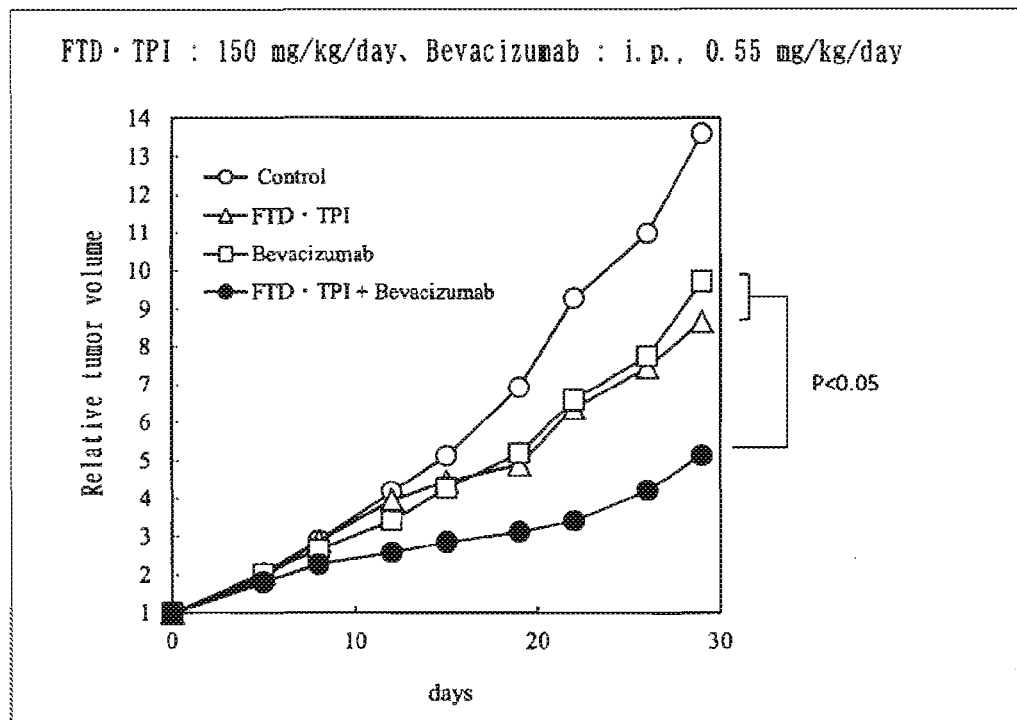
FIG. 3 is a figure illustrating the combinatorial effect of an FTD/TPI combination drug and bevacizumab with respect to colon cancer.
Figure 4:
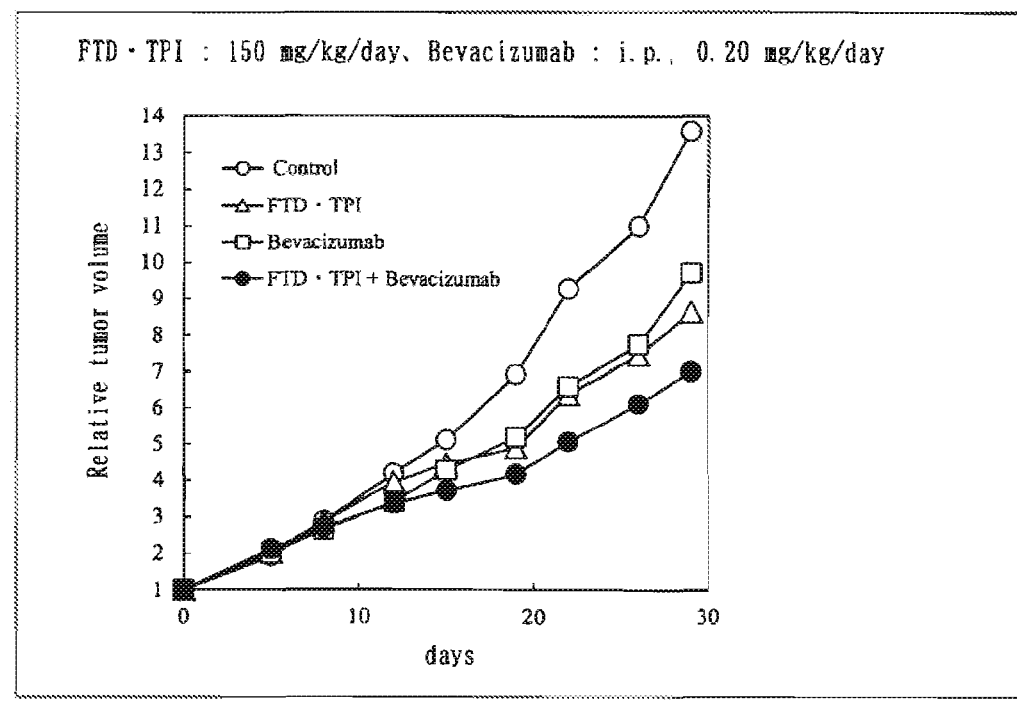
FIG. 4 is a figure illustrating the combinatorial effect of an FTD/TPI combination drug and bevacizumab with respect to colon cancer.

The antitumor agent of the present invention is characterized in that an FTD/TPI combination drug and an anti-VEGF antibody or anti-EGFR antibody are administered in combination. Another antitumor agent may be further administered in combination as long as the FTD/TPI combination drug and the anti-VEGF antibody or anti-EGFR antibody are administered in combination.

FTD and TPI in the present invention are known compounds, respectively, and can be synthesized, for example, in accordance with the method described in the pamphlet of WO 96/30346 A. In addition, a combination drug containing FTD and TPI at a molar ratio of 1:0.5 is also known (Non-Patent Literatures 1 and 2).

VEGF recognized by the "anti-VEGF antibody" in the present invention may be any one of VEGF-A, VEGF-B, VEGF-C, VEGF-D, VEGF-D, VEGF-E, PLGF (placental growth factor)-1 and PLGF-2, which are of human VEGF family, and is preferably human VEGF-A. The base sequence and the amino acid sequence of human VEGF-A are registered as the accession numbers NM001171623 and NP001165094, respectively in GenBank, and information of these sequences may be used in the present invention.

EGFR recognized by the "anti-EGFR antibody" in the present invention is preferably human EGFR. Meanwhile, the base sequence and the amino acid sequence of human EGFR are, registered as the accession numbers NM005228 and NP005219, respectively in GenBank, and information of these sequences may be used in the present invention.

In addition, the "anti-VEGF antibody" and the "anti-EGFR antibody" in the present invention may be a monoclonal antibody or may be a polyclonal antibody, or may be an antibody fragment such as Fab, Fab' and F(ab')$_2$. Furthermore, the anti-VEGF antibody may be an extracellular domain of the VEGF receptor.

In addition, the origin of these antibodies is preferably a human chimeric antibody, a humanized antibody or a human antibody from the viewpoint of reducing the immunogenicity.

The "anti-VEGF antibody" and the "anti-EGFR antibody" in the present invention can be usually manufactured in accordance with a method for manufacturing an antibody known in the field. A commercially available antibody may be also used.

The "anti-VEGF antibody" in the present invention is not particularly limited if it is an antibody specifically recognizing VEGF, and exemplified by bevacizumab, aflibercept, ranibizumab and icrucumab, and is preferably bevacizumab. Commercially available products may be also used as these antibodies.

The "anti-EGFR antibody" in the present invention is not particularly limited if it is an antibody specifically recognizing EGFR, and exemplified by cetuximab, panitumumab, matuzumab, nimotuzumab, zalutumumab and necitumumab, and is preferably cetuximab or panitumumab. Commercially available products may be also used as these antibodies.

The daily dose of the FTD/TPI combination drug in the antitumor agent of the present invention on the administration day is preferably from 17 to 115%, more preferably from 50 to 100%, more preferably from 70 to 100%, and particularly preferably 100% to the recommended dose in the case of single administration of the FTD/TPI combination drug to a cancer patient from the viewpoint of the action of enhancing the antitumor effect of the anti-VEGF antibody or anti-EGFR antibody by the FTD/TPI combination drug. Specifically, the dose of the FTD/TPI combination drug is preferably from 11 to 80 mg/m$^2$/day, more preferably from 35 to 70 mg/m$^2$/day, more preferably from 50 to 70 mg/m$^2$/day, and particularly preferably 70 mg/m$^2$/day as FTD.

The daily dose of bevacizumab in the antitumor agent of the present invention on the administration day is preferably from 4 to 100%, more preferably from 11 to 100%, and particularly preferably from 34 to 100% to the recommended dose in the case of single administration of bevacizumab to a cancer patient from the viewpoint of the action of enhancing the antitumor effect by the FTD/TPI combination drug. Specifically, the dose of bevacizumab is preferably from 0.4 to 15 mg/kg/day, more preferably from 0.4 to 10 mg/kg/day, more preferably from 1.10 to 10 mg/kg/day, and particularly preferably from 3.4 to 10 mg/kg/day.

The daily dose of cetuximab in the antitumor agent of the present invention on the administration day is preferably from 4 to 100%, more preferably from 11 to 100%, and particularly preferably from 50 to 100% to the recommended dose in the case of single administration of cetuximab to a cancer patient from the viewpoint of the action of enhancing the antitumor effect of cetuximab by the FTD/TPI combination drug. Specifically, the dose of cetuximab is preferably from 15 to 400 mg/m$^2$/day, more preferably from 44 to 400 mg/m$^2$/day, and particularly preferably from 200 to 400 mg/m$^2$/day.

The daily dose of panitumumab in the antitumor agent of the present invention on the administration day is preferably from 4 to 100%, more preferably from 11 to 100%, and particularly preferably from 34 to 100% to the recommended dose in the case of single administration of panitumumab to a cancer patient from the viewpoint of the action of enhancing the antitumor effect of panitumumab by the FTD/TPI combination drug. Specifically, the daily dose of panitumumab is preferably from 0.23 to 6 mg/kg/day, more preferably from 0.67 to 6 mg/kg/day, and particularly preferably from 2.03 to 6 mg/kg/day.

The "administration in combination" in the present invention means that the FTD/TPI combination drug and an anti-VEGF antibody or anti-EGFR antibody are administered in combination within a certain period within a range of achieving the effect of the present invention of enhancing the antitumor effect of an anti-VEGF antibody or anti-EGFR antibody while suppressing outbreak of adverse effects. Specific administration schedule of the antitumor agent of the present invention can be suitably selected depending on, for example, carcinoma or stage of disease. The administration schedule of the FTD/TPI combination drug is preferably five day administration every day and two day withdrawal that is repeated twice, and then two week withdrawal. The administration schedule of the anti-VEGF antibody or anti-EGFR antibody is preferably administration once every one to three weeks. Such administration schedule may be implemented once, or repeated twice or more.

Examples of the target cancer of the antitumor agent of the present invention include specifically head and neck cancer, digestive cancer (for example, esophageal cancer, gastric cancer, duodenal cancer, liver cancer, bile duct cancer (for example, gallbladder or bile duct cancer), pancreatic cancer, small intestinal cancer, and colon cancer (for example, colorectal cancer, colon cancer and rectal cancer)), lung cancer, breast cancer, ovary cancer, uterine cancer (for example, cervical cancer and corpus uteri cancer), renal cancer, bladder cancer, and prostatic cancer. Among them, the target cancer of the antitumor agent of the present invention is preferably digestive cancer, lung cancer or breast cancer, more preferably colorectal cancer, lung cancer, breast cancer, pancreatic cancer, or gastric cancer, and particularly preferably colorectal cancer from the viewpoint of the antitumor effect and the adverse effects. The cancer herein includes not only cancers at a primary lesion, but also cancers spread to other organs (for example, liver). In addition, the antitumor agent of the present invention may be used in postoperative adjuvant chemotherapy performed for preventing relapse after surgical extraction of the tumor, or may be a pre-operative adjuvant chemotherapy previously performed for surgical extraction of the tumor.

The antitumor agent of the present invention is formulated in multiple dosage forms separately for each active ingredient since the administration means and administration schedules are different by each active ingredient and all active ingredients cannot be formulated together in one dosage form. It is preferred that FTD and TPI are formulated as a combination drug, and the anti-VEGF antibody and anti-EGFR antibody as a single active ingredient preparation.

Each preparation may be produced and sold together in one package suitable for administration in combination, or each preparation may be produced and sold in a separate package respectively as long as each active ingredient is administered according to the dose of the present invention.

The dosage form of the antitumor agent of the present invention is not particularly limited, and can be suitably selected depending on the therapeutic purpose. Examples of the dosage form of the antitumor agent of the present invention include specifically an oral agent (for example, a tablet, a coated tablet, a powder, a granule, a capsule, and a liquid), an injection, a suppository, a patch, and an ointment. The FTD/TPI combination drug is preferably an oral agent, and the anti-VEGF antibody and anti-EGFR antibody is preferably an injection, and particularly preferably an injection for intravenous administration.

The antitumor agent of the present invention can be usually prepared according to a known method using pharmaceutically acceptable carriers depending on the dosage form thereof. Examples of such carrier include various carriers generally used in conventional drugs, for example an excipient, a binder, a disintegrator, a lubricant, a diluent, a solubilizer, a suspending agent, a tonicity agent, a pH adjusting agent, a buffer, a stabilizer, a colorant, a flavoring agent, and an odor improving agent.

In addition, the present invention also relates to an antitumor effect enhancer including an FTD/TPI combination drug for enhancing the antitumor effect of an anti-VEGF antibody or anti-EGFR antibody in a cancer patient (particularly, patient with colorectal cancer). The antitumor effect enhancer has the dosage form of the antitumor agent described above.

The present invention also relates to an antitumor agent including an FTD/TPI combination drug for treating a cancer patient administered with an anti-VEGF antibody or anti-EGFR antibody (particularly, a patient with colorectal cancer). The antitumor agent has the dosage form described above.

The present invention also relates to a kit preparation including an FTD/TPI combination drug and an instruction manual describing that the FTD/TPI combination drug is administered in combination with an anti-VEGF antibody or anti-EGFR to a cancer patient (particularly, a patient with colorectal cancer). The "instruction manual" herein may describe the dose described above, preferably recommending the dose described above, whether it is legally bound or not. Specifically, examples of the instruction manual include a package insert, and a pamphlet. In addition, the instruction manual in the kit preparation including the instruction manual may be embedded by printing onto the package of the kit preparation, or may be enclosed along with the antitumor agent in the package of the kit preparation.

The present invention also relates to a method for treating a cancer, which is characterized by administering an FTD/TPI combination drug and an anti-VEGF antibody or anti-EGFR in combination. The antitumor agent containing an FTD/TPI combination drug and an anti-VEGF antibody or anti-EGFR has the dosage form of the antitumor agent described above.

EXAMPLES

Next, the present invention will be further described with Examples and Reference Examples more specifically.

Reference Example

The culture cells of a human colon cancer cell line (KM20C) ($1 \times 10^7$ cells/mouse) were transplanted into the abdominal cavity of a five to six week-old BALB/cA icl-nu mouse. The mouse was allocated into each group such that the average weight of each group was equal, and the day when the grouping (n=10) was implemented was assumed to be Day 0.

An FTD/TPI combination drug (a mixture of FTD and TPI at a molar ratio of 1:0.5) was prepared to give 75, 100, 150, 300 and 450 mg/kg/day as FTD. The drug administration was initiated from Day 3, and oral administration of the FTD/TPI combination drug for five days every day and two day withdrawal were performed for six weeks.

As an index of the antitumor effect, the number of the surviving mice in each group was checked, and the survival time of each group was compared. The results are shown in Table 1.

TABLE 1

| Drug | Dose (mg/kg/day) | Treatment[a] | No. of animals | Survival time (day) Mean ± SD | ILS[b] (%) |
|---|---|---|---|---|---|
| Control | — | — | 10 | 40.0 ± 4.3 | — |
| FTD/TPI combination drug | 75 | Five day oral administration with two day rest (b.i.d) | 10 | 50.0 ± 9.1 | 25.0 |
| FTD/TPI combination drug | 100 | Five day oral administration with two day rest (b.i.d) | 10 | 75.8 ± 42.6 | 89.5 |
| FTD/TPI combination drug | 150 | Five day oral administration with two day rest (b.i.d) | 10 | 125.7 ± 64.8 | 214.3 |
| FTD/TPI combination drug | 300 | Five day oral administration with two day rest (b.i.d) | 10 | 75.6 ± 17.5 | 89.0 |
| FTD/TPI combination drug | 450 | Five day oral administration with two day rest (b.i.d) | 10 | 54.1 ± 18.3 | 35.3 |

[a]Drugs were given for 6 weeks from Day 3.
[b]ILS means increase in life span.
ILS (%) = [(mean survival time of treatment group)/(mean survival time of control group) − 1] × 100

As described in Table 1, in the mice, the survival time was longer in the group of 150 mg/kg/day as FTD for the FTD/TPI combination drug. From this, the recommending dose (RD) of the FTD/TPI combination drug in a mouse is 150 mg/kg/day as FTD. In contrast, RD of the FTD/TPI combination drug in human is 70 mg/m$^2$/day as FTD. From this, 150 mg/kg/day in a mouse corresponds to 70 mg/m$^2$/day in human.

With bevacizumab, the doses of 1.25 and 5, 20 mg/kg were administered into the abdominal cavity for three weeks every seven days using nude mice transplanted with a human breast cancer cell line MX-1, and the optimal dose was studied. From the report (Bevacizumab Interview Form) that 5 mg/kg gave the highest tumor growth inhibition rate, and the effect reached the peak at a higher dose than the dose, RD of bevacizumab in a mouse is 5 mg/kg/day. In contrast, RD of bevacizumab in human is 10 mg/kg/day. From this, 5 mg/kg/day in a mouse corresponds to 10 mg/kg/day in human.

With cetuximab, the doses of 0.5 and 1 mg/dose were injected intravenously for five weeks every three days using nude mice transplanted with a human renal cell cancer cell line SK-RC-29, and the optimal dose was studied. From the report (Clinical cancer research (1998) 4, 2957-2966) that 1 mg/dose (corresponding to 40 mg/kg when the weight of mouse is assumed to be 25 g) gave the highest tumor growth inhibition rate, RD of cetuximab in a mouse is 40 mg/kg/day. In contrast, RD of cetuximab in human is 400 mg/m$^2$/day. From this, 40 mg/kg/day in a mouse corresponds to 400 mg/m$^2$/day in human.

With panitumumab, the doses of 20, 200, 500 and 1000 g/dose were injected intravenously twice every week for five weeks using nude mice transplanted with a human colon cancer cell line HT29, and the optimal dose was studied. From the report (Panitumumab Interview Form) that the effect reached the peak at a dose equal to or higher than 200 g/dose (corresponding to 8 mg/kg when the weight of a mouse is assumed to be 25 g), RD of panitumumab in a mouse is 8 mg/kg. In contrast, RD of panitumumab in human is 6 mg/kg/day. From this, accordingly, 8 mg/kg/day in a mouse corresponds to 6 mg/kg/day in human.

Example 1

A human colon cancer cell line (KM20C) was transplanted onto the right chest of a five to six week-old BALB/cA Jcl-nu mouse. The length (mm) and the breadth (mm) of the tumor after the tumor transplantation were measured, and the tumor volume (TV) was calculated. Then, the mouse was allocated into each group such that the average TV in each group was equal, and the day when the grouping (n=6 to 7) was implemented was assumed to be Day 0.

The administration dose of the drug was 10 mL/kg, and the FTD/TPI combination drug (a mixture of FTD and TPI at a molar ratio of 1:0.5) was prepared to be 150 mg/kg/day as the dose of FTD. Bevacizumab (Avastin injection, Chugai Pharmaceutical Co., Ltd.) was prepared to be 0.20, 0.55, 1.7 and 5 mg/kg/day.

The FTD/TPI combination drug was orally administered on Days 1 to 14 every day, and bevacizumab was administered into the abdominal cavity for two weeks at a frequency of twice a week from Day 1. To the combination-treated group, the FTD/TPI combination drug and bevacizumab were administered in the same doses and the same administration schedules as those of the single agent-treated group.

As an index of the antitumor effect, the TV in each group was calculated, and the relative tumor volume (RTV) for Day 0 was obtained from the equation below and plotted. The chronological changes of RTV were compared among no treatment group (control), an FTD/TPI combination drug-treated group, a bevacizumab-treated group, and a FTD/TPI combination drug and bevacizumab combination-treated group. In addition, the weight loss as the toxicity was evaluated. The results are shown in Table 2 and FIGS. 1 to 4.

$$TV(mm^3) = (length \times breadth^2)/2$$

$$RTV = (TV\ on\ evaluation\ day)/(TV\ on\ Day\ 0)$$

TABLE 2

| Drug | Dose (mg/kg/day) | RTV[a] (mean ± SD) | IR[b] (%) | Body weight change[c] (%, mean ± SD) |
|---|---|---|---|---|
| Control | — | 13.58 ± 3.54 | — | 1.3 ± 5.2 |
| FTD/TPI combination drug | 150 | 8.65 ± 3.03 | 36.3 | −4.9 ± 4.6 |
| Bevacizumab | 0.20 | 8.93 ± 2.79 | 34.3 | 9.7 ± 5.1 |
| Bevacizumab | 0.55 | 9.71 ± 4.99 | 28.5 | 3.2 ± 6.0 |
| Bevacizumab | 1.7 | 8.19 ± 2.29 | 39.7 | 5.2 ± 6.7 |
| Bevacizumab | 5 | 8.34 ± 1.82 | 38.6 | 1.8 ± 4.6 |
| FTD/TPI combination drug + Bevacizumab | 150 + 0.20 | 7.01 ± 2.17 | 48.4 | −7.2 ± 7.4 |
| FTD/TPI combination drug + Bevacizumab | 150 + 0.55 | 5.13 ± 0.62*# | 62.2 | −5.2 ± 5.7 |
| FTD/TPI combination drug + Bevacizumab | 150 + 1.7 | 5.43 ± 1.31*# | 60.1 | −2.6 ± 6.0 |
| FTD/TPI combination drug + Bevacizumab | 150 + 5 | 5.11 ± 1.90*## | 62.4 | −3.7 ± 9.4 |

*p < 0.05 by one-sided Welch's test as compared to the FTD-PI alone group.
,##p < 0.05, p < 0.01 by one-sided Welch's test as compared to the Bevacizumab alone group.
[a]Relative tumor volume (RTV) on Day 29 was calculated as the ratio of TV on Day 29 to that on Day 0 according to the following formula: RTV = (TV on Day 29)/(TV on Day 0)
[b]Tumor growth inhibition rate (IR) on Day 29 on the basis of RTV was calculated according to the following formula: IR (%) = [1 − (mean RTV of the treated group)/(mean RTV of the control group)] × 100
[c]BW change (%; mean) on Day 29 was calculated according to the following formula: BWC (%) = [(BW on Day 29) − (BW on Day 0)]/(BW on Day 0) × 100

Figure 5:
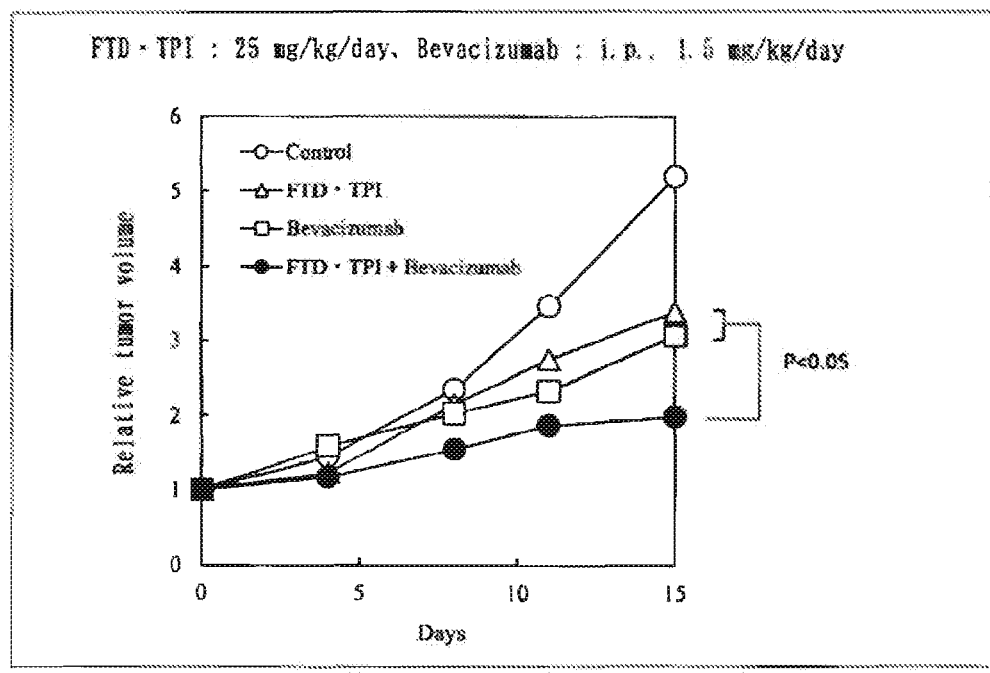
FIG. 5 is a figure illustrating the combinatorial effect of an FTD/TPI combination drug and bevacizumab with respect to colon cancer.
Figure 6:
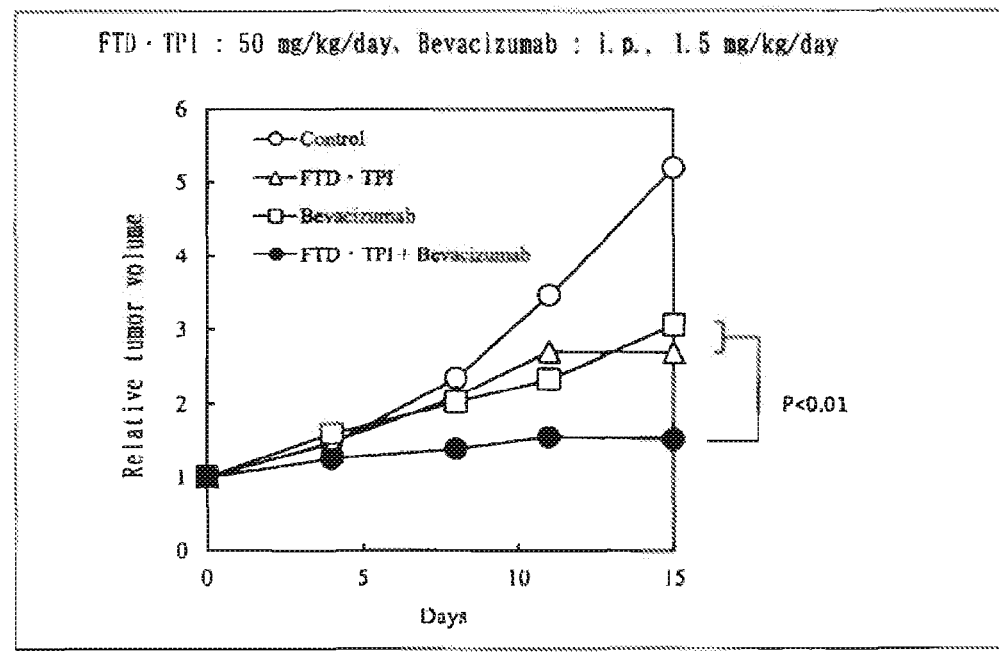
FIG. 6 is a figure illustrating the combinatorial effect of an FTD/TPI combination drug and bevacizumab with respect to colon cancer.
Figure 7:
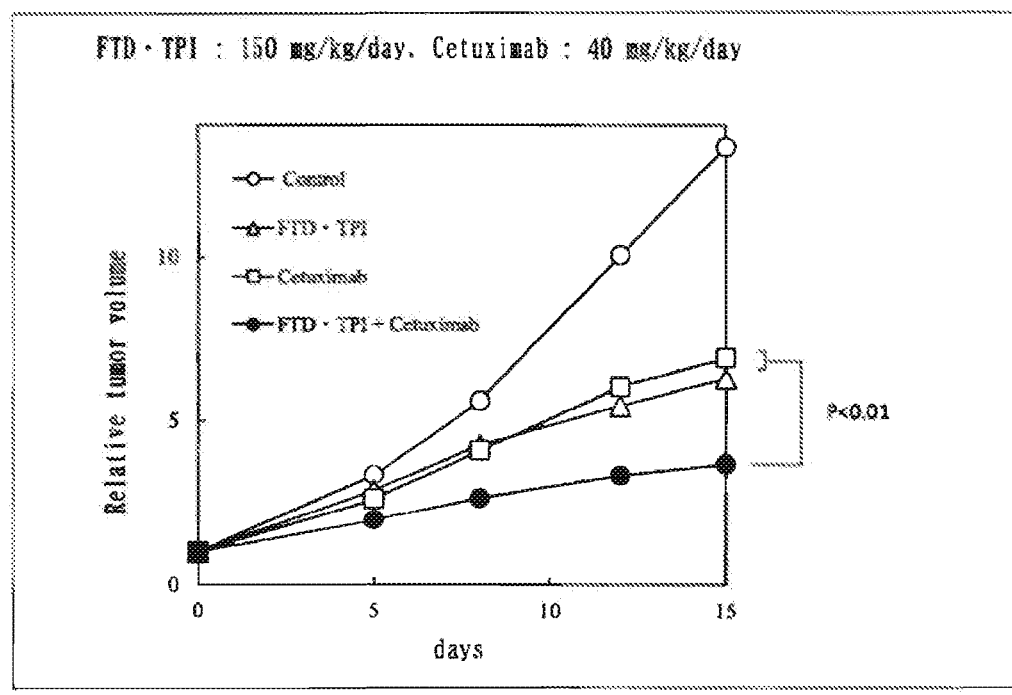
FIG. 7 is a figure illustrating the combinatorial effect of an FTD/TPI combination drug and cetuximab with respect to colon cancer.
Figure 8:
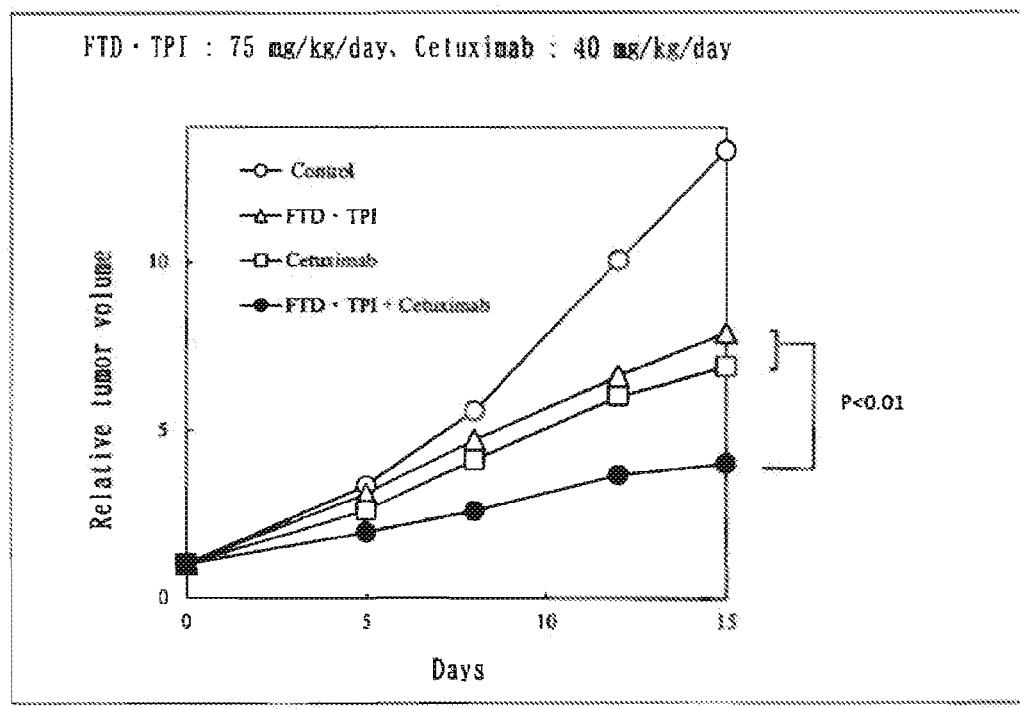
FIG. 8 is a figure illustrating the combinatorial effect of an FTD/TPI combination drug and cetuximab with respect to colon cancer.
Figure 9:
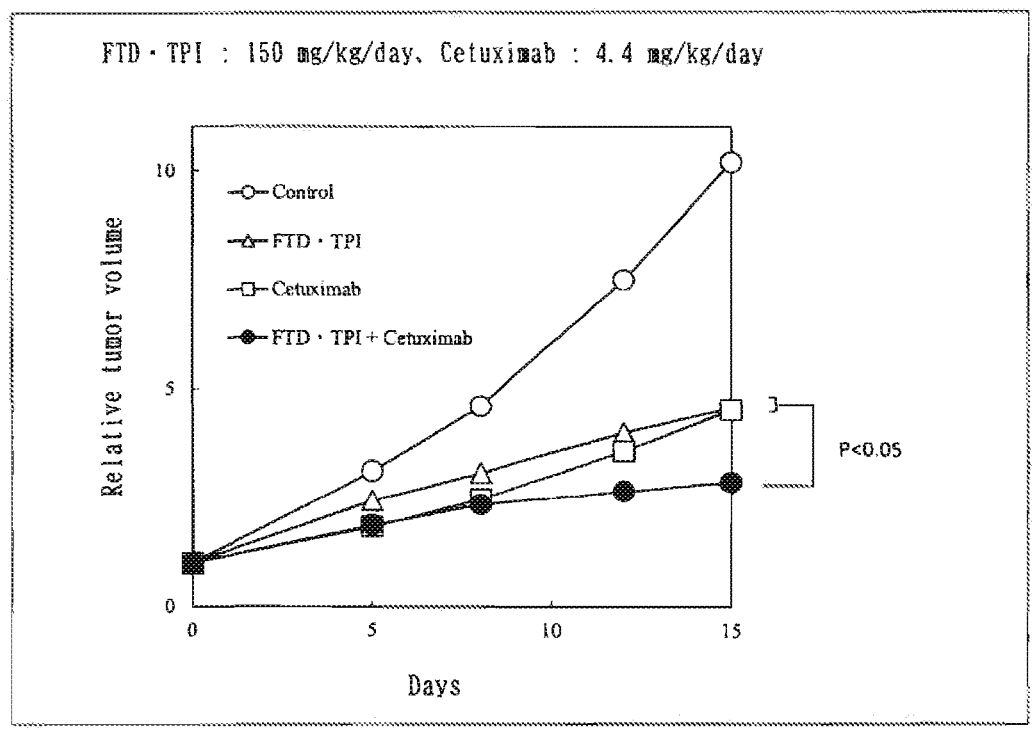
FIG. 9 is a figure illustrating the combinatorial effect of an FTD/TPI combination drug and cetuximab with respect to colon cancer.
Figure 10:
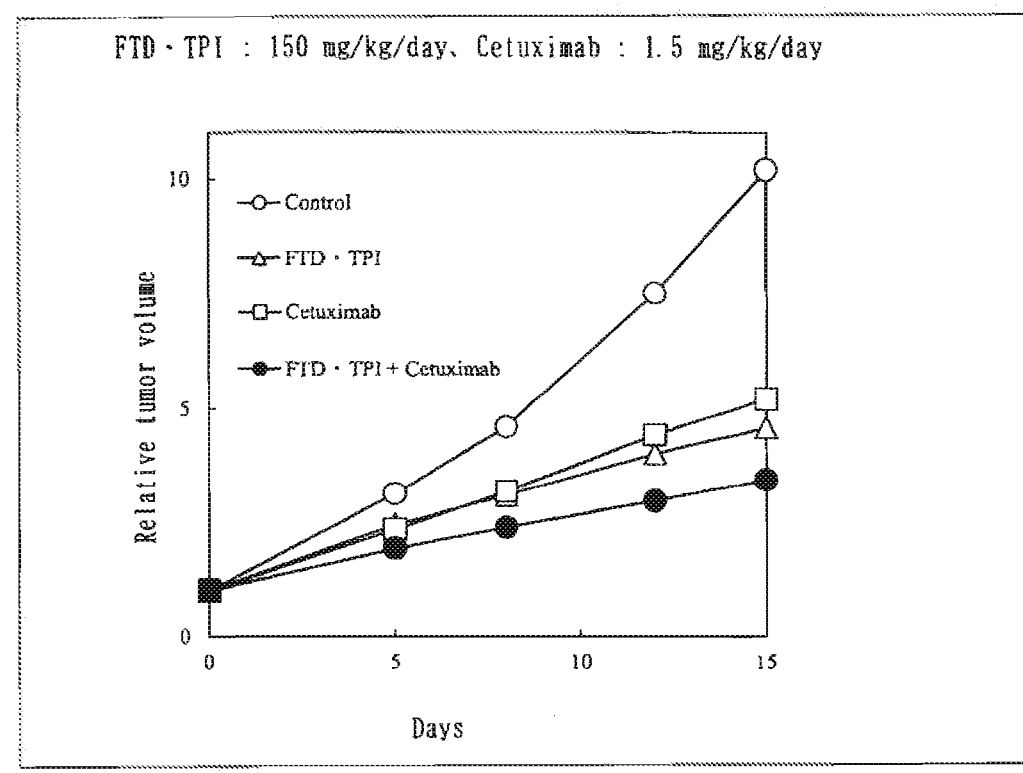
FIG. 10 is a figure illustrating the combinatorial effect of an FTD/TPI combination drug and cetuximab with respect to colon cancer.

Next, a test was performed in the same manner using a human breast cancer cell line (MC-2). Here, the FTD/TPI combination drug (a mixture of FTD and TPI at a molar ratio of 1:0.5) was prepared to be 25 and 50 mg/kg/day as the dose of FTD, and bevacizumab was prepared to be 1.5 mg/kg/day. The results are shown in Table 3 and FIGS. 5 to 6.

TABLE 3

| Drug | Dose (mg/kg/day) | RTV[a] (mean ± SD) | IR[b] (%) | Body weight change[c] (%, mean ± SD) |
|---|---|---|---|---|
| Control | — | 5.20 ± 1.43 | — | 12.0 ± 2.7 |
| FTD/TPI combination drug | 25 | 3.39 ± 0.52 | 34.7 | 7.1 ± 1.9 |
| FTD/TPI combination drug | 50 | 2.70 ± 0.26 | 48.1 | 7.9 ± 1.8 |
| Bevacizumab | 1.5 | 3.06 ± 0.88 | 41.1 | 7.7 ± 3.7 |

TABLE 3-continued

| Drug | Dose (mg/kg/day) | RTV[a] (mean ± SD) | IR[b] (%) | Body weight change[c] (%, mean ± SD) |
|---|---|---|---|---|
| FTD/TPI combination drug + Bevacizumab | 25 + 1.5 | 1.99 ± 0.70**,# | 61.7 | 9.1 ± 2.9 |
| FTD/TPI combination drug + Bevacizumab | 50 + 1.5 | 1.52 ± 0.16**,## | 70.8 | 8.6 ± 1.2 |

**p < 0.01 by student's t-test as compared to the FTD·TPI alone group.
,##p < 0.05, p < 0.01 by student's t-test as compared to the Bevacizumab alone group.
[a]Relative tumor volume (RTV) on Day 15 was calculated as the ratio of TV on Day 15 to that on Day 0 according to the following formula: RTV = (TV on Day 15)/(TV on Day 0)
[b]Tumor growth inhibition rate (IR) on Day 15 on the basis of RTV was calculated according to the following formula: IR (%) = [1 − (mean RTV of the treated group)/(mean RTV of the control group)] × 100
[c]BW change (%; mean) on Day 15 was calculated according to the following formula: BWC (%) = [(BW on Day 15) − (BW on Day 0)]/(BW on Day 0) × 100

As shown in Tables 2 to 3 and FIGS. 1 to 6, remarkable enhancement for the antitumor effect was seen when the FTD/TPI combination drug was 25 to 150 mg/kg/day (corresponding to 11 to 70 mg/m$^2$/day in human) as FTD, and bevacizumab was 0.20 to 5 mg/kg/day (corresponding to 0.40 to 10 mg/kg/day in human), and statistically significant synergistic antitumor effect was obtained when bevacizumab was 0.55 to 5 mg/kg/day (corresponding to 1.10 to 10 mg/kg/day in human).

Any treated group showed an acceptable degree of the weight loss, and no increase of the adverse effect was found caused by the administration in combination. In the test using KM20C, the weight loss was found to be −4.9% in the FTD/TPI combination drug-treated group while it was found to be −2.6 to −3.7% in the combination FTD/TPI combination drug-treated group and 1.7 to 5 mg/kg/day of bevacizumab combination-treated group, and thus the weight loss decreased. Also in the test using MC-2, similar results were obtained. Whereas administration antitumor agents in combination usually increase adverse effects as the antitumor effect increases, with the present invention, adverse effects decreases while the antitumor effect increases, which is a very surprising result.

In addition, the effect of delaying tumor growth by concomitant use of the FTD/TPI combination drug was checked (Clin Cancer Res. 2000; 6(2): 701-8.; J Radiat Res. 2007; 48(3): 187-95.; Invest New Drugs. 2008; 26(1): 1-5.; J Radiat Res. 2011; 52(5): 646-54.). With respect to the time period during which the tumor volume doubled from Day 0 (namely, RTV becomes 2), the results of the combination-treated group were predicted from the single agent-treated group of FIGS. 5 and 6. The "length of days till RTV actually reached 2" of the single agent-treated group were summarized in Table 4. The "length of days till RTV actually reached 2" was calculated under the assumption that RTV on the measurement day when RTV firstly exceeded 2 changes according to a linear function from RTV on the measurement day immediately before the day.

TABLE 4

| FTD/TPI combination drug (mg/kg/day) | Bevacizumab (mg/kg/day) | Length of Days (day) |
|---|---|---|
| 25 | 0 | 7.35 |
| 50 | 0 | 7.33 |
| 0 | 1.5 | 7.71 |

Table 5 summarizes the "expected length of days" for RTV of the combination-treated group to reach 2, and the "actual length of days" for RTV to reach 2.

TABLE 5

| FTD/TPI combination drug (mg/kg/day) | Bevacizumab (mg/kg/day) | Expected length of days (day) | Actual length of days (day) |
|---|---|---|---|
| 25 | 1.5 | 15.07 | 15.11 |
| 50 | 1.5 | 15.05 | 26.25 |

Particularly, in the combination-treated group where the FTD/TPI combination drug was 50 mg/kg/day and bevacizumab was 1.5 mg/kg/day, the "actual length of days" till RTV reached 2 were 7.33 days and 7.71 days in each of the single agent-treated groups. Accordingly, under the assumption that the actions and effects of the FTD/TPI combination drug and bevacizumab are not antagonistic, the "expected length of days" till RTV reached 2 in the combination-treated group was 15.05 days, which is the sum of the time periods. However, the "actual length of days" till RTV reached 2 was, surprisingly, 26.25 days. These results show that the action of enhancing the antitumor effect of bevacizumab by the FTD/TPI combination drug is synergistic.

Example 2

A human colon cancer cell line (Co-3) was transplanted onto the right chest of a five to six week-old BALB/cA Jcl-nu mouse. The length (mm) and the breadth (mm) of the tumor after the tumor transplantation were measured, and the tumor volume (TV) was calculated. Then, the mouse was allocated into each group such that the average TV in each group was equal, and the day when the grouping (n=3 to 7) was implemented was assumed to be Day 0.

The administration dose of the drug was 10 mL/kg, and the FTD/TPI combination drug (a mixture of FTD and TPI at a molar ratio of 1:0.5) was prepared to be 75, 150 mg/kg/day as the dose of FTD. Cetuximab (ERBITUX injection, Merck Serono Co., Ltd.) was prepared to be 1.5, 4.4 and 40 mg/kg/day. The FTD/TPI combination drug was orally administered on Days 1 to 14 every day, and cetuximab was administered into the abdominal cavity for 2 weeks at a frequency of twice a week from Day 1. To the combination-treated group, the FTD/TPI combination drug and cetuximab were administered in the same doses and the same administration schedules as those of the single agent-treated group.

As an index of the antitumor effect, TV on Days 5, 8, 12 and 15 in each group was calculated, and the relative tumor volume (RTV) for Day 0 was obtained according to the formula of Example 1 and plotted. The chronological changes of RTV were compared of no treatment group (control), the FTD/TPI combination drug-treated group, and the cetuximab-treated group and the FTD/TPI combination drug and cetuximab combination-treated group. In addition, the weight loss as the toxicity was evaluated. The results are shown in Tables 6 to 7 and FIGS. 7 to 10.

TABLE 6

| Drug | Dose (mg/kg/day) | RTV[a] (mean ± SD) | IR[b] (%) | Body weight change[c] (%, mean ± SD) |
|---|---|---|---|---|
| Control | — | 13.33 ± 4.10 | — | −5.2 ± 4.5 |
| FTD/TPI combination drug | 75 | 7.91 ± 1.73 | 40.6 | −10.6 ± 6.4 |
| FTD/TPI combination drug | 150 | 6.27 ± 0.97 | 53.0 | −13.2 ± 7.0 |
| Cetuximab | 40 | 6.90 ± 2.52 | 48.2 | 0.2 ± 2.8 |
| FTD/TPI combination drug + Cetuximab | 75 + 40 | 4.01 ± 0.37**### | 69.9 | −5.5 ± 4.7 |
| FTD/TPI combination drug + Cetuximab | 150 + 40 | 3.69 ± 0.32**### | 72.3 | −5.0 ± 4.2 |

**$p < 0.01$ by student's t-test as compared to the FTD·TPI alone group.
$p < 0.01$ by student's t-test as compared to the Cetuximab alone group.
[a]Relative tumor volume (RTV) on Day 15 was calculated as the ratio of TV on Day 15 to that on Day 0 according to the following formula: RTV = (TV on Day 15)/(TV on Day 0)
[b]Tumor growth inhibition rate (IR) on Day 15 on the basis of RTV was calculated according to the following formula: IR (%) = [1 − (mean RTV of the treated group)/(mean RTV of the control group)] × 100
[c]BW change (%; mean) on Day 15 was calculated according to the following formula: BWC (%) = [(BW on Day 15) − (BW on Day 0)]/(BW on Day 0) × 100

TABLE 7

| Drug | Dose (mg/kg/day) | RTV[a] (mean ± SD) | IR[b] (%) | Body weight change[c] (%, mean ± SD) |
|---|---|---|---|---|
| Control | — | 10.19 ± 4.70 | — | −2.5 ± 6.4 |
| FTD/TPI combination drug | 150 | 4.58 ± 1.39 | 55.1 | −18.6 ± 4.2 |
| Cetuximab | 1.5 | 4.50 ± 1.18 | 55.9 | −2.1 ± 4.8 |
| Cetuximab | 4.4 | 4.53 ± 1.32 | 55.6 | −0.2 ± 5.9 |
| FTD/TPI combination drug + Cetuximab | 150 + 1.5 | 3.42 ± 0.72 | 66.4 | −9.4 ± 5.6 |
| FTD/TPI combination drug + Cetuximab | 150 + 4.4 | 2.88 ± 0.63*# | 71.7 | −14.9 ± 5.1 |

*$p < 0.05$ by one-sided Welch's test as compared to the FTD·TPI alone group.
$p < 0.05$ by one-sided Welch's test as compared to the Cetuximab alone group.
[a]Relative tumor volume (RTV) on Day 15 was calculated as the ratio of TV on Day 15 to that on Day 0 according to the following formula: RTV = (TV on Day 15)/(TV on Day 0)
[b]Tumor growth inhibition rate (IR) on Day 15 on the basis of RTV was calculated according to the following formula: IR (%) = [1 − (mean RTV of the treated group)/(mean RTV of the control group)] × 100
[c]BW change (%; mean) on Day 15 was calculated according to the following formula: BWC (%) = [(BW on Day 15) − (BW on Day 0)]/(BW on Day 0) × 100

Figure 11:
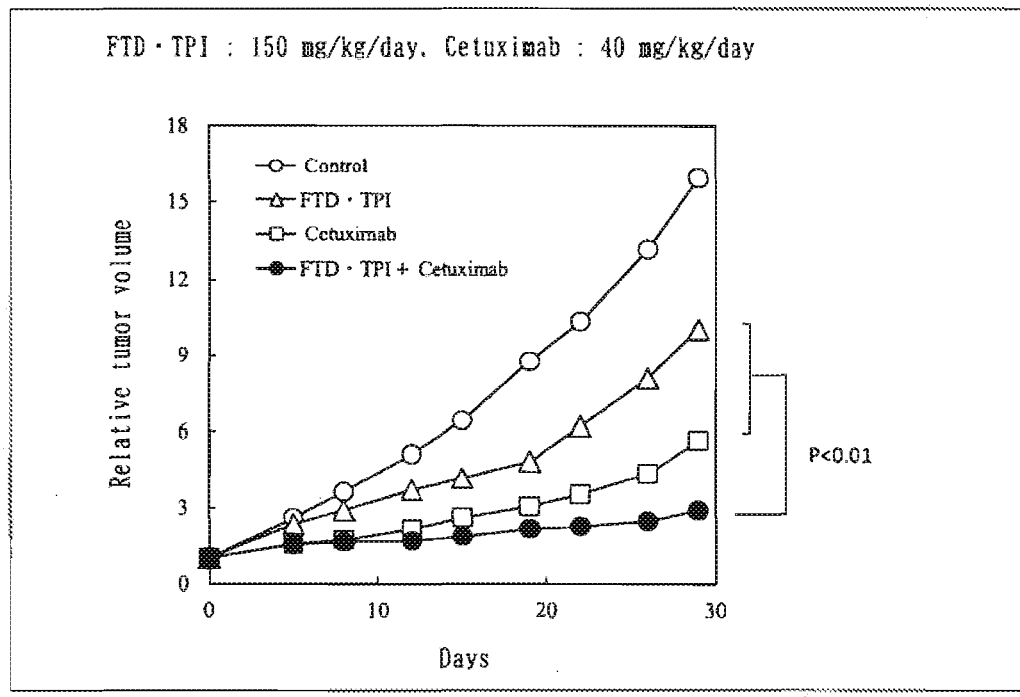
FIG. 11 is a figure illustrating the combinatorial effect of an FTD/TPI combination drug and cetuximab with respect to colon cancer.
Figure 12:
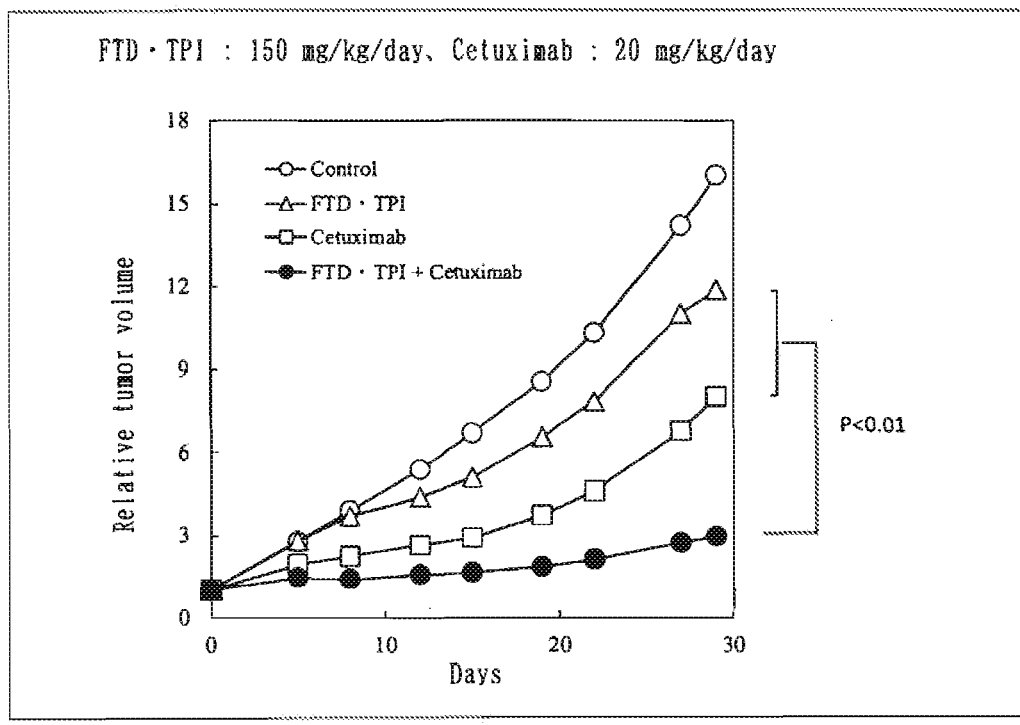
FIG. 12 is a figure illustrating the combinatorial effect of an FTD/TPI combination drug and cetuximab with respect to colon cancer.
Figure 13:
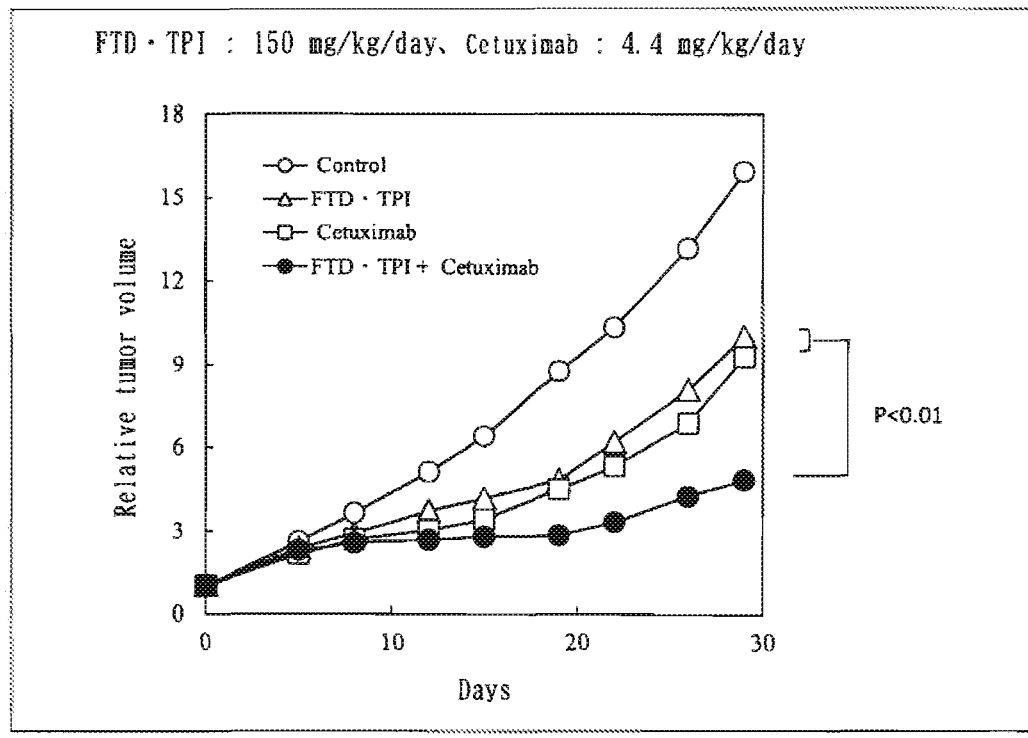
FIG. 13 is a figure illustrating the combinatorial effect of an FTD/TPI combination drug and cetuximab with respect to colon cancer.
Figure 14:
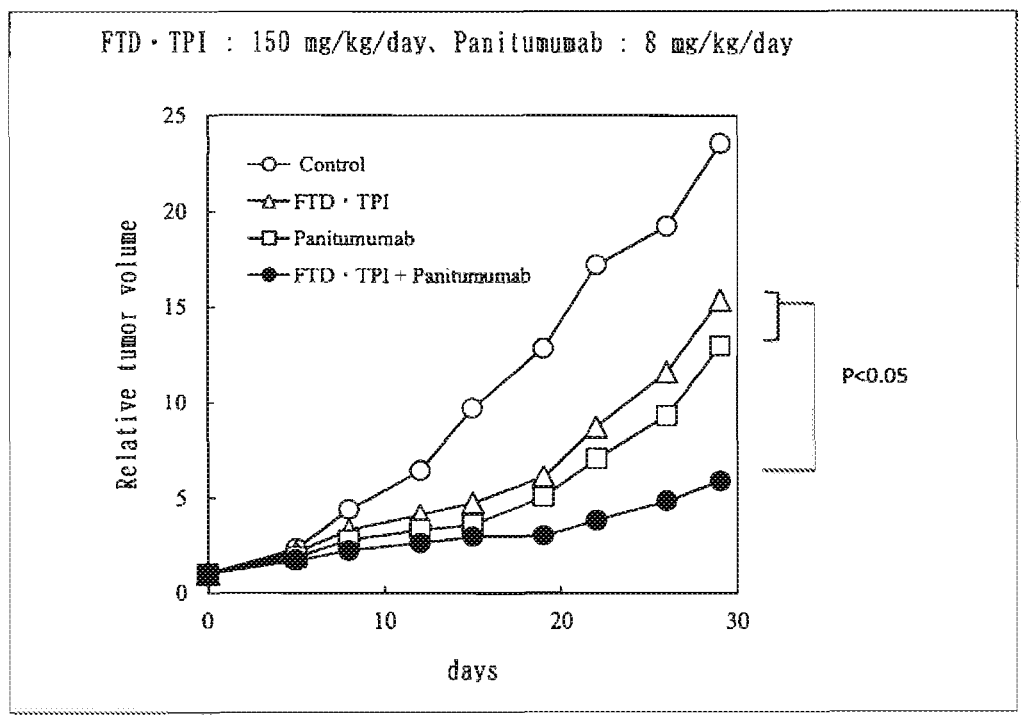
FIG. 14 is a figure illustrating the combinatorial effect of an FTD/TPI combination drug and panitumumab with respect to colon cancer.
Figure 15:
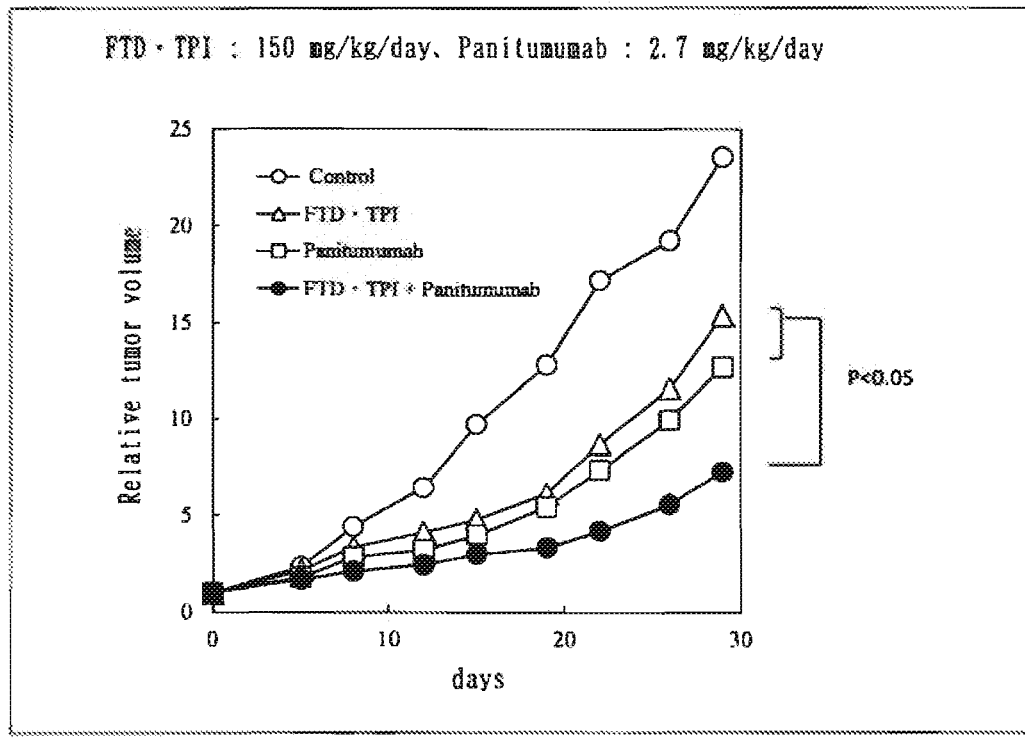
FIG. 15 is a figure illustrating the combinatorial effect of an FTD/TPI combination drug and panitumumab with respect to colon cancer.
Figure 16:
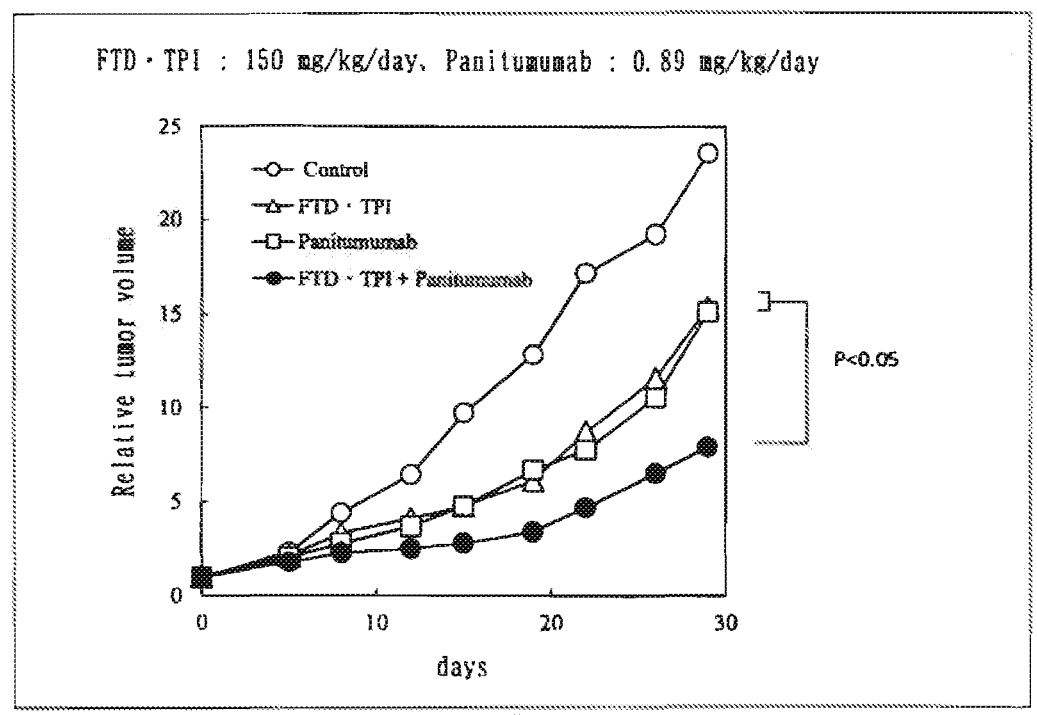
FIG. 16 is a figure illustrating the combinatorial effect of an FTD/TPI combination drug and panitumumab with respect to colon cancer.
Figure 17:
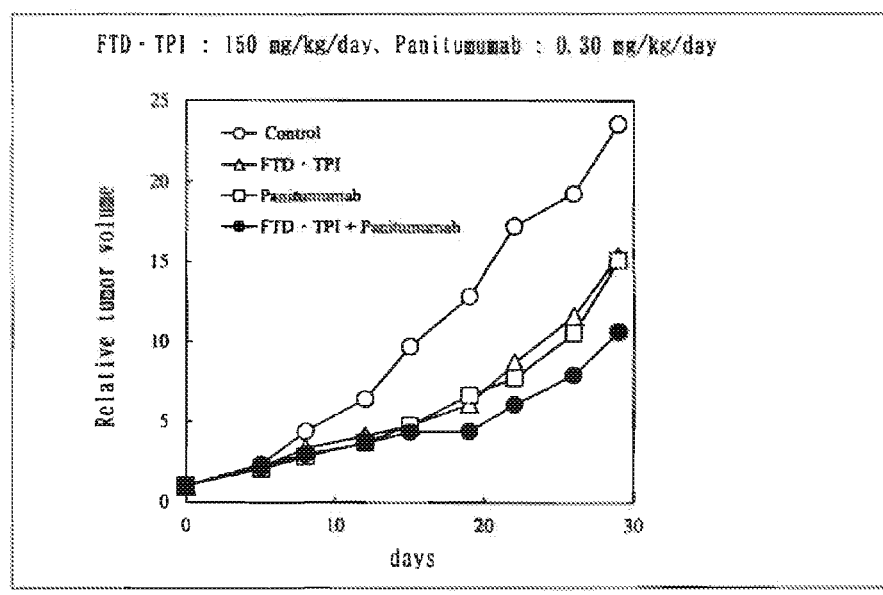
FIG. 17 is a figure illustrating the combinatorial effect of an FTD/TPI combination drug and panitumumab with respect to colon cancer.

Next, a test was performed in the same manner using a human colon cancer cell line (SW48). Here, cetuximab was prepared to be 4.4, 20 and 40 mg/kg/day. The results are shown in Tables 8 to 9 and FIGS. 11 to 13.

TABLE 8

| Drug | Dose (mg/kg/day) | RTV[a] (mean ± SD) | IR[b] (%) | Body weight change[c] (%, mean ± SD) |
|---|---|---|---|---|
| Control | — | 15.95 ± 4.54 | — | 8.6 ± 5.6 |
| FTD/TPI combination drug | 150 | 10.05 ± 3.22 | 37.0 | −5.3 ± 1.9 |
| Cetuximab | 4.4 | 9.29 ± 2.79 | 41.7 | 11.6 ± 4.7 |
| Cetuximab | 40 | 5.65 ± 1.71 | 64.6 | 10.5 ± 5.0 |
| FTD/TPI combination drug + Cetuximab | 150 + 4.4 | 4.85 ± 0.46**## | 69.6 | 3.6 ± 3.4 |
| FTD/TPI combination drug + Cetuximab | 150 + 40 | 2.92 ± 0.89**## | 81.7 | 5.4 ± 5.1 |

**$p < 0.01$ by Student's t test as compared to the FTD·TPI alone group.
$p < 0.01$ by Student's t test as compared to the Cetuximab alone group.
[a]Relative tumor volume (RTV) on Day 29 was calculated as the ratio of TV on Day 29 to that on Day 0 according to the following formula: RTV = (TV on Day 29)/(TV on Day 0)
[b]Tumor growth inhibition rate (IR) on Day 29 on the basis of RTV was calculated according to the following formula: IR (%) = [1 − (mean RTV of the treated group)/(mean RTV of the control group)] × 100
[c]BW change (%; mean) on Day 29 was calculated according to the following formula: BWC (%) = [(BW on Day 29) − (BW on Day 0)]/(BW on Day 0) × 100

TABLE 9

| Drug | Dose (mg/kg/day) | RTV[a] (mean ± SD) | IR[b] (%) | Body weight change[c] (%, mean ± SD) |
|---|---|---|---|---|
| Control | — | 16.03 ± 7.17 | — | −2.5 ± 9.5 |
| FTD/TPI combination drug | 150 | 11.87 ± 3.27 | 25.9 | −2.2 ± 6.5 |
| Cetuximab | 20 | 8.01 ± 3.66 | 50.1 | 9.9 ± 12.0 |
| FTD/TPI combination drug + Cetuximab | 150 + 20 | 2.96 ± 0.81**## | 81.6 | 5.1 ± 5.4 |

**$p < 0.01$ by Student's t test as compared to the FTD·TPI alone group.
$p < 0.01$ by Student's t test as compared to the Cetuximab alone group.
[a]Relative tumor volume (RTV) on Day 29 was calculated as the ratio of TV on Day 29 to that on Day 0 according to the following formula: RTV = (TV on Day 29)/(TV on Day 0)
[b]Tumor growth inhibition rate (IR) on Day 29 on the basis of RTV was calculated according to the following formula: IR (%) = [1 − (mean RTV of the treated group)/(mean RTV of the control group)] × 100
[c]BW change (%; mean) on Day 29 was calculated according to the following formula: BWC (%) = [(BW on Day 29) − (BW on Day 0)]/(BW on Day 0) × 100

As shown in Tables 6 to 9 and FIGS. 7 to 13, remarkable enhancement for the antitumor effect was seen when the FTD/TPI combination drug was 75 to 150 mg/kg/day (corresponding to 35 to 70 mg/m$^2$/day in human) as FTD, and cetuximab was 1.5 to 40 mg/kg/day (corresponding to 15 to 400 mg/m$^2$/day in human) and statistically significant synergistic antitumor effect was obtained when cetuximab was 4.4 to 40 mg/kg/day (corresponding to 44 to 400 mg/m$^2$/day in human).

In addition, any treated group had an acceptable degree of the weight loss, and no increase of the adverse effect was found from the administration in combination. In the test using Co-3, the weight loss was found to be −13.2% (or −18.6%) in the 150 mg/kg/day FTD/TPI combination drug-treated group, and the weight loss was found to be −5.0% (or −9.4 to −14.9%) in the 150 mg/kg/day FTD/TPI combination drug and 1.5 to 40 mg/kg/day cetuximab combination-treated group, and thus the weight loss decreased. Also in the test using SW48, similar results were obtained. Whereas administration of antitumor agents in combination ordinarily increases adverse effects as the antitumor effect increases, with the present invention, adverse effects decreases while the antitumor effect increases, which is a very surprising result.

In addition, the effect of delaying tumor growth by concomitant use of the FTD/TPI combination drug was checked (Clin Cancer Res. 2000; 6(2): 701-8.; J Radiat Res. 2007; 48(3): 187-95.; Invest New Drugs. 2008; 26(1): 1-5.; J Radiat Res. 2011; 52(5): 646-54.). With respect to the time period during which the tumor volume doubled from Day 0 (namely, RTV becomes 2), the results of the combination-treated group were predicted from the single agent-treated group of FIGS. 11 and 13. The "length of days till RTV actually reached 2" of the single agent-treated group were summarized in Table 10. The "length of days till RTV actually reached 2" was calculated under the assumption that RTV on the measurement day when RTV firstly exceeded 2 changes according to a linear function from RTV on the measurement day immediately before the day.

TABLE 10

| FTD/TPI combination drug (mg/kg/day) | Cetuximab (mg/kg/day) | Length of Days (day) |
|---|---|---|
| 150 | 0 | 3.62 |
| 0 | 4.4 | 4.32 |
| 0 | 40 | 10.34 |

Table 11 summarizes the expected length of days for RTV of combination-treated group to reach 2, and the actual length of days for RTV to reach 2.

TABLE 11

| FTD/TPI combination drug (mg/kg/day) | Cetuximab (mg/kg/day) | Expected length of days (day) | Actual length of days (day) |
|---|---|---|---|
| 150 | 4.4 | 7.94 | 13.66 |
| 150 | 40 | 13.96 | 16.68 |

In the combination-treated group where the FTD/TPI combination drug was 150 mg/kg/day and cetuximab was 4.4 mg/kg/day, the "actual length of days" when RTV reached 2 in each of the single agent-treated groups were 3.62 days and 4.32 days. Accordingly, the "expected length of days" till RTV reached 2 in the combination-treated group was 7.94 days, which is the sum of the time periods under the assumption that the actions and effects of the FTD/TPI combination drug and cetuximab are not antagonistic. However, the "actual length of days" till RTV reached 2 was surprisingly 13.66 days. In addition, the "expected length of days" till RTV reached 2 in the combination-treated group where the FTD/TPI combination drug was 150 mg/kg/day and cetuximab was 20 mg/kg/day, was obtained in the same manner from FIG. 12, which was 8.50 days. The "actual length of days" till RTV reached 2 was 20.70 days. These results show that the action of enhancing the antitumor effect of cetuximab by the FTD/TPI combination drug is synergistic.

Example 3

A human colon cancer cell line (Co-3) was transplanted onto the right chest of a five to six week-old BALB/cA Jcl-nu mouse. The length (mm) and the breadth (mm) of the tumor after the tumor transplantation were measured, and the tumor volume (TV) was calculated. Then, the mouse was allocated into each group such that the average TV in each group was equal, and the day when the grouping (n=6) was implemented was assumed to be Day 0.

The administration dose of the drug was 10 mL/kg, and the FTD/TPI combination drug (a mixture of FTD and TPI at the molar ratio of 1:0.5) was prepared to be 150 mg/kg/day as the dose of FTD. Panitumumab (Vectibix (registered trademark) injection, Amgen Inc.) was prepared to be 0.30, 0.89, 2.7 and 8 mg/kg/day. The FTD/TPI combination drug was orally administered on Days 1 to 14 every day, and panitumumab was administered into the abdominal cavity for two weeks at a frequency of twice a week from Day 1. To the combination-treated group, the FTD/TPI combination drug and panitumumab were administered in the same doses and the same administration schedules as those of the single agent-treated group.

As an index of the antitumor effect, TV on Days 5, 8, 12 and 15 was calculated in each group, and the relative tumor volume (RTV) for Day 0 was obtained according to the formula of Example 1 and plotted. The chronological changes of RTV were compared of no treatment group (control), the FTD/TPI combination drug-treated group, the panitumumab-treated group and the combination FTD/TPI combination drug and panitumumab treated group. In addition, the weight loss as the toxicity was evaluated. The results are shown in Table 12 and FIGS. 14 to 17.

TABLE 12

| Drug | Dose (mg/kg/day) | RTV[a] (mean ± SD) | IR[b] (%) | Body weight change[c] (%, mean ± SD) |
|---|---|---|---|---|
| Control | — | 23.58 ± 11.81 | — | −12.8 ± 6.0 |
| FTD/TPI combination drug | 150 | 15.38 ± 3.10 | 34.8 | −16.2 ± 2.3 |
| Panitumumab | 0.30 | 18.15 ± 6.79 | 23.0 | −11.3 ± 5.3 |

TABLE 12-continued

| Drug | Dose (mg/kg/day) | RTV[a] (mean ± SD) | IR[b] (%) | Body weight change[c] (%, mean ± SD) |
|---|---|---|---|---|
| Panitumumab | 0.89 | 15.10 ± 7.51 | 35.9 | −6.7 ± 4.3 |
| Panitumumab | 2.7 | 12.71 ± 4.37 | 46.1 | −1.2 ± 3.1 |
| Panitumumab | 8 | 12.97 ± 2.33 | 45.0 | −4.5 ± 4.5 |
| FTD/TPI combination drug + Panitumumab | 150 + 0.30 | 10.66 ± 3.84[#] | 54.8 | −16.2 ± 5.3 |
| FTD/TPI combination drug + Panitumumab | 150 + 0.89 | 7.92 ± 1.77**[#] | 66.4 | −10.6 ± 5.0 |
| FTD/TPI combination drug + Panitumumab | 150 + 2.7 | 7.27 ± 1.80**[*#] | 69.2 | −9.7 ± 6.3 |
| FTD/TPI combination drug + Panitumumab | 150 + 8 | 5.90 ± 1.96**[*##] | 75.0 | −8.7 ± 4.4 |

**p < 0.01 by one-sided Welch's test as compared to the FTD·TPI alone group.
[#], [##]p < 0.05, p < 0.01 by one-sided Welch's test as compared to the Panitumumab alone group.
[a]Relative tumor volume (RTV) on Day 29 was calculated as the ratio of TV on Day 29 to that on Day 0 according to the following formula: RTV = (TV on Day 29)/(TV on Day 0)
[b]Tumor growth inhibition rate (IR) on Day 29 on the basis of RTV was calculated according to the following formula: IR (%) = [1 − (mean RTV of the treated group)/(mean RTV of the control group)] × 100
[c]BW change (%; mean) on Day 29 was calculated according to the following formula: BWC (%) = [(BW on Day 29) − (BW on Day 0)]/(BW on Day 0) × 100

As shown in Table 12 and FIGS. 14 to 17, remarkable enhancement for the antitumor effect was seen when the dose of FTD/TPI combination drug was 150 mg/kg/day (corresponding to 70 mg/m²/day in human) as FTD and panitumumab was 0.3 to 8 mg/kg/day (corresponding to 0.23 to 6 mg/kg/day in human), and statistically significant synergistic antitumor effect was obtained when panitumumab was 0.89 to 8 mg/kg/day (corresponding to 0.67 to 6 mg/kg/day in human).

In addition, any treated group showed an acceptable degree of the weight loss, and no increase of the adverse effect was found caused by the administration in combination. The weight loss was found to be −16.2% in the FTD/TPI combination drug-treated group, and the weight loss was found to be 8.7 to 10.6% in the combination FTD/TPI combination drug and 0.89 to 8 mg/kg/day panitumumab combination-treated group, and thus the weight loss decreased. Whereas administration of antitumor agents in combination ordinarily increases adverse effects as the antitumor effect increases, but with the present invention, adverse effects decreases while the antitumor effect increases, which is a very surprising result.

From above, it was revealed that the FTD/TPI combination drug remarkably enhances the antitumor effect of bevacizumab, cetuximab or panitumumab while suppressing outbreak of adverse effects.

The invention claimed is:

1. A method for treating a cancer, comprising:
administering to a subject in need thereof 17 to 115% of a recommended daily dose of a combination drug comprising trifluridine and tipiracil hydrochloride at a molar ratio of 1:0.5, and 11 to 100% of a recommended daily dose of an antibody selected from the group consisting of bevacizumab, cetuximab, and panitumumab, in combination.

2. The method of claim 1, wherein the antibody is bevacizumab.

3. The method of claim 1, wherein the antibody is cetuximab.

4. The method of claim 1, wherein the cancer is at least one selected from the group consisting of colorectal cancer, lung cancer, breast cancer, pancreatic cancer, and gastric cancer.

5. The method of claim 1, wherein the antibody is panitumumab.

6. A method for treating a cancer, comprising:
administering to a subject in need thereof 11 to 80 mg/m²/day of a combination drug comprising trifluridine and tipiracil hydrochloride at a molar ratio of 1:0.5, and 1.10 to 10 mg/kg/day of bevacizumab, in combination.

7. A method for treating a cancer, comprising:
administering to a subject in need thereof 11 to 80 mg/m²/day of a combination drug comprising trifluridine and tipiracil hydrochloride at a molar ratio of 1:0.5, and 44 to 400 mg/m²/day of cetuximab, in combination.

8. A method for treating a cancer, comprising:
administering to a subject in need thereof 11 to 80 mg/m²/day of a combination drug comprising trifluridine and tipiracil hydrochloride at a molar ratio of 1:0.5, and 0.68 to 6 mg/kg/day of panitumumab, in combination.

9. The method of claim 6, wherein a daily dose of the combination drug is from 17 to 115% of a recommended daily dose of the combination drug alone, and a daily dose of bevacizumab is from 11 to 100% of a recommended daily dose of bevacizumab alone.

10. The method of claim 7, wherein a daily dose of the combination drug is from 17 to 115% of a recommended daily dose of the combination drug alone, and a daily dose of cetuximab is from 11 to 100% of a recommended daily dose of cetuximab alone.

11. The method of claim 8, wherein a daily dose of the combination drug is from 17 to 115% of a recommended daily dose of the combination drug alone, and a daily dose of panitumumab is from 11 to 100% of a recommended daily dose of panitumumab alone.

12. The method of claim 6, wherein 35 to 70 mg/m²/day of the combination drug is administered to the subject.

13. The method of claim 6, wherein the combination drug is administered such that 70 mg/m²/day of trifluridine is administered to the subject.

14. The method of claim 7, wherein 35 to 70 mg/m²/day of the combination drug is administered to the subject.

15. The method of claim 7, wherein the combination drug is administered such that 70 mg/m²/day of trifluridine is administered to the subject.

16. The method of claim 8, wherein 35 to 70 mg/m²/day of the combination drug is administered to the subject.

17. The method of claim 8, wherein the combination drug is administered such that 70 mg/m²/day of trifluridine is administered to the subject.

18. The method of claim 6, wherein the cancer is at least one selected from the group consisting of colorectal cancer, lung cancer, breast cancer, pancreatic cancer, and gastric cancer.

19. The method of claim 7, wherein the cancer is at least one selected from the group consisting of colorectal cancer, lung cancer, breast cancer, pancreatic cancer, and gastric cancer.

20. The method of claim 8, wherein the cancer is at least one selected from the group consisting of colorectal cancer, lung cancer, breast cancer, pancreatic cancer, and gastric cancer.

* * * * *